(12) United States Patent
Cash

(10) Patent No.: US 11,357,541 B2
(45) Date of Patent: Jun. 14, 2022

(54) PROTECTIVE BUBBLE

(71) Applicant: Phillip Cash, Dalton, GA (US)

(72) Inventor: Phillip Cash, Dalton, GA (US)

(*) Notice: Subject to any disclaimer, the term of this patent is extended or adjusted under 35 U.S.C. 154(b) by 590 days.

(21) Appl. No.: 16/379,938

(22) Filed: Apr. 10, 2019

(65) Prior Publication Data

US 2020/0323554 A1    Oct. 15, 2020

(51) Int. Cl.
*A61B 17/34* (2006.01)
*A61M 39/02* (2006.01)
*A61M 39/06* (2006.01)

(52) U.S. Cl.
CPC ..... *A61B 17/3423* (2013.01); *A61M 39/0247* (2013.01); *A61B 17/3415* (2013.01); *A61B 2017/3419* (2013.01); *A61M 2039/0279* (2013.01); *A61M 2039/0673* (2013.01)

(58) Field of Classification Search
CPC ................. A61M 39/0247; A61M 2039/0288
See application file for complete search history.

(56) References Cited

U.S. PATENT DOCUMENTS

| | | | | |
|---|---|---|---|---|
| 2,367,690 | A * | 1/1945 | Edgarh | A61F 15/006 128/888 |
| 5,116,324 | A * | 5/1992 | Brierley | A61M 25/02 128/DIG. 6 |
| 8,454,603 | B2 * | 6/2013 | Webb | A61B 17/60 606/59 |
| 2005/0182455 | A1 * | 8/2005 | Thrope | A61N 1/32 607/48 |
| 2013/0231619 | A1 * | 9/2013 | Wiltshire | A61F 13/02 604/305 |
| 2019/0388652 | A1 * | 12/2019 | Albany | A61M 25/02 |
| 2021/0369492 | A1 * | 12/2021 | O'Grady | A61M 39/0247 |

* cited by examiner

*Primary Examiner* — Nicholas W Woodall
(74) *Attorney, Agent, or Firm* — Miller & Martin PLLC; Stephen J. Stark

(57) ABSTRACT

A bubble for use with various medical equipment or other sites on the body such as IV ports, feeding tube locations, PODs, CGMs (Continuous Glucose Monitors) or other equipment connected to the body, whereby the bubble assists in protecting the site, and hopefully prevents medical equipment from being dislodged, if installed, to provide for strenuous activity or even application of water, such as bathing, showering, etc.

10 Claims, 4 Drawing Sheets

PROTECTIVE BUBBLE

FIELD OF THE INVENTION

The present invention relates to a protective bubble that an individual could place on their body to at least assist in providing a water-resistant, if not water proof, bubble over one of an insulin pump, POD or CGM (continuous glucose monitor), feeding tube, or IV port, on the body of an individual such as on their arm, leg, torso or other location during sports or wet events, such as bathing, swimming, etc.

BACKGROUND OF THE INVENTION

Insulin pumps have been around for many years. Connecting an insulin pump to a body has been the subject of numerous efforts over the years. More recently PODs have been introduced which is a smaller insulin pump typically with only a few days of insulin which normally provides an adhesive strip to attach the pod to the body of the user. Unfortunately, during sporting events, such as those which might involve physical contact, or strenuous sweating, or other activities as well, such as swimming or other water related activities, PODs tend to be dislodged, and for such events such as swimming in the ocean, can be lost.

At least one company has attempted to solve the problem at Pumpwear.com by providing a three inch wide spandex band for use in wearing over pods or sensors such as CGMs to attempt to keep them secure. They are normally sized by the arm diameter such as (a) eight to ten inch arms size for a small child, (b) ten to thirteen inch, (c) fourteen to seventeen inch, (d) sixteen to twenty-one inch, or (e) twenty-two to twenty-six inch. Accordingly, based on the size of the individual wearing the band, one of at least six different sizes can be provided. Furthermore, specific sizes are advertised as available upon request. All designs are three inch wide stretchy bands about the arm of an individual with no other structure which covers over the pod or monitor. The pre-determined resiliency and pre-determined diameter, relative to a portion of the body where the band attaches, are the only ways to select a fit of the band relative to a POD and/or user.

While this structure might be able to keep some PODs from becoming lost, they certainly are not normally waterproof and the POD may become dislodged internal to the band during strenuous activity and/or swimming. This would then require re-inserting the needle to deliver insulin. Furthermore, this type of construction does not lend itself to cover a multiple attachment locations, such as an arm, torso or leg of a user. Furthermore, the user would appear to be stuck with the design provided on the band. In order to have a new design, a new band would need to be provided. Additionally, the website of Pumpwear.com advises that when ordering these bands that "bands are made to be snug so that they keep pods and sensors secure, however it is your responsibility as the user to insure the pods and sensor do not come off and Pumpwear, Inc. is not responsible for sensors or pods that come lose."

Additionally, patients in hospitals are often sponge bathed if they have feeding tubes or IV ports. Many of these patients long for, or would greatly benefit from, having a bath or shower.

Accordingly, there is a perceived need for improved constructions in the marketplace.

SUMMARY OF THE INVENTION

Accordingly, it is an object of a presently preferred embodiment of the present invention to provide an improved bubble for providing a water tight bubble over at least one of an IV port, feeding tube connection, continuous glucose monitor, pod and/or insulin pump on the body of a user preferably in an attached manner;

It is also an object of many embodiments of the present invention to provide an improved compartment which can provide at least a water-resistant, if not waterproof cavity, against the skin of a user about an attached medical device to thereby assist in reducing the amount of water onto the device (such as one of an IV port, feeding tube connection, POD, CGM insulin pump, or other device) during sports, strenuous activity and/or wet use.

It is also an object of many embodiments of the present invention to provide an improved device for providing a water tight cavity about a feeding tube or other connection, IV port, installed pod, continuous glucose monitor and/or insulin pump on a person with an attached bubble adhered the skin of the user.

It is an object of many embodiments of the present invention to provide a cover which can adhere to a location on the body of a person.

Accordingly, in accordance with presently preferred embodiments of the present invention, a bubble or cover structure is provide which provides at least a water-resistant, but often water-proof, seal relative to the skin of a user with a perimeter preferably about or relative to a perimeter of a medical device having a needle or other structure stuck into the skin of a user such as one of a feeding tube connection, IV port, POD, CGM or insulin pump (other devices, any deliver glucose, chemotherapy or other medication or check other blood parameters with similar devices), whereby the cover can provide at least a water-resistant, if not a waterproof, seal together with the skin to assist in not only retaining the device within the structure, preferably in a water-resistant, if not waterproof, manner, so as to prevent the device from being lost, but also assist in maintaining the device in position in an installed configuration with the needle connected to the device inserted by the person's skin, preferably internally to the cover. The cover may also be utilized to cover over other structure such as wounds or other structure.

The bubble can be connected to the skin in a number of ways. It is envisioned that the bubble has a base which connects the cover to at least one of a portion of the person whether that be an arm, a torso, or a leg of an individual, although certain other body parts could at least assist in connecting the structure to the body of a user as well, such as by adhering to the skin of the user.

For some embodiments an adhesive layer is connected to the base of the bubble. A release strip may be initially provided over the adhesive layer to maintain the adhesive nature of the strip. The release strip may be removed by the user and the base, with the adhesive layer, placed in contact with the skin over a desired site so that the adhesive layer forms a seal about the site, preferably in a water-tight manner to provide a cavity about the site which is water proof.

The cover may take a variety of forms whether as a hard material and/or a flexible material depending on the application. Many preferred embodiments will utilize a flexible cover, but others could be more or less rigid.

Some embodiments may utilize belts or bands to retain the goggle to a body part. Belts and bands may take various forms.

For many embodiments, the adhesive utilized is a waterproof adhesive that may or may not be water soluble. Some of these embodiments utilize alcohol to remove the adhesive once applied. Additionally, at least some embodiments have a release pull, such as formed into the bubble, so that in an emergency, or even just to assist in removal, the release pull can be pulled (while still leaving the base attached to the skin) to access the site internal to the bubble.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
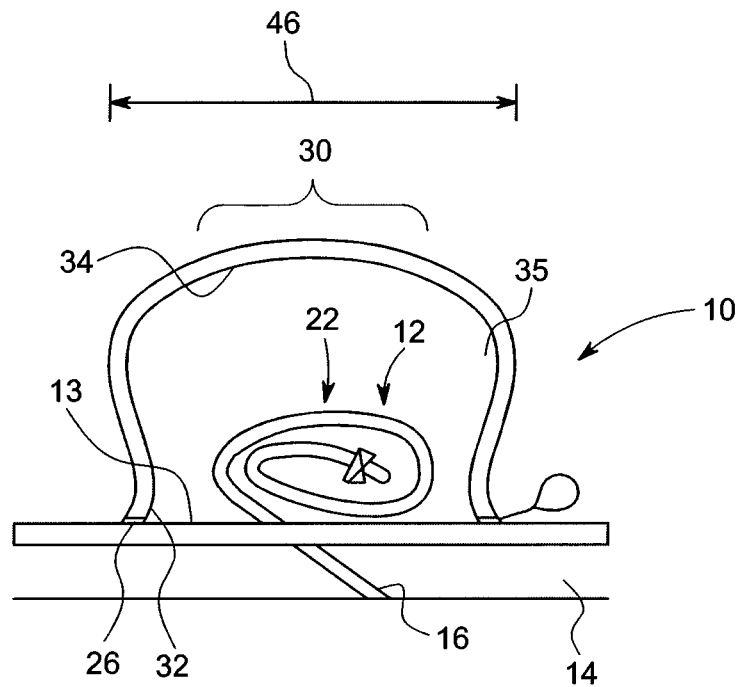
FIG. 1 is a cross sectional view of a presently preferred embodiment of the present invention with a medical device shown in phantom inside connected to a user.

The figures show a protective bubble illustrated as a goggle or bubble 10 having a construction calculated to at least assist in protecting a medical device 12 or other item, such as a wound, etc. at a site 13. Medical devices 12 usually have a penetration through the skin 14 of a user, such as illustrated. Medical devices 12 could be a feeding tube connection, an IV port, insulin pumps, PODs, Continuous Glucose Monitors (CGMs), chemotherapy pumps, glucose pumps and/or other delivery and/or sensor systems, some of which have penetrations such as a needle 16 extending into the skin 14. For this application, "connected medical devices' are defined as medical devices 12 having a continuous penetration through the skin 14 and are connected to a supply or monitoring apparatus like a pump, glucose monitor, etc. . . . . . "Disconnected medical devices" could refer to feeding tubes, IV ports, and the like, which are disconnected from a source, and need to be re-attached to be functional.

Goggle 10 preferably provides a cover 20 which may take a variety of forms but some embodiments preferably extend above an outer or upper most surface 22 of the medical device 12 and/or site and extend to an inner perimeter 32, possibly of a foot 26, which may, or may not directly contact the skin 14 at a base 25, depending upon the embodiment. Base 25 may be at least initially planar for many embodiments. Inner perimeter 32 is preferably pre-determined in shape for many embodiments. Cover 20 may be transparent or translucent to be able to see the medical device 12, when installed (which could be helpful to be able to read a number or other indicia, such as a reading on the CGM or other medical device 12), or not. Cover 20 may also be at least partially flexible or rigid, depending upon the embodiment. Cover 20 may also be transparent or translucent in some embodiments to view the medical device 12 (such as to verify there are no current issues).

Foot 26 may directly contact skin 14 for some embodiments, it may not for other embodiments. Foot 26 and/or base 25 may have adhesive layer 27 initially protected with release strip 28. Release strip 28 may be removed to expose the adhesive layer 27 which may be applied about the site 13 and/or medical device 12.

Foot 26, as illustrated, may be able to contact skin 14 and assist in forming a water resistant, if not water proof, seal with the skin 14 about at least the penetration at the inner perimeter 32 which is preferably a predetermined configuration and might be substantially circular, as illustrated, or other shape, illustrated as needle 16, if not about an inner perimeter 32 of the foot 26 about the medical device 12 to provide an air cavity 35 about, and preferably at least partially above, the device 12 and or site 13 and internal areas of the cover 20 relative to the skin 14. The cover 20 may have a predetermined configuration to facilitate maintaining the air cavity 35 about the medical device 12 when installed as well. The cover 20 is preferably non-planar with the base 25 and, in fact, even if pressed against the base 25, material would remain so that a flat planar sheet could not be provided for many embodiments.

Since many medical devices, such as PODs are stuck onto the skin, having the cover contact the skin 14 at a first pre-determined perimeter 30 of the medical device 12 can keep the medical device 12 secured to the skin 14 as it is designed to do. Inner surface 34 of cover 20 may contact the upper most surface 22 of the device, or not, such as by being spaced by gap 35 above upper most surface 22 while the cover 20 may still surround the medical device 12 with the skin 14.

Adhesive layer 27 may be selected from appropriate adhesives, whether water soluble, or not. Some adhesive layers 27 may not be soluble in water, but could be soluble with other solvents, such as alcohol, etc.

The covers 20 may, or may not, be manufactured to cooperate with specific medical devices 12 such as by having an inner surface 50 calculated to either contact or not contact the medical 12 at certain locations and/or be appropriately spaced therefrom. Of course, covers 20 could be at least somewhat generic to the medical device(s) they retain.

The span 46 of the cover 20 is illustrated extending beyond the perimeter 30 of the medical device 12 (and possibly beyond perimeter 32 of foot 26), particularly if the cover 20 is compressed against the base 25 to be parallel with the base 25. Cover 20 can be provided with a predetermined shape with the air cavity 35 about the medical device 12 maintained in that predetermined shape for many embodiments. For many embodiments, this construction differs from a planar sheet with a seal about an exterior perimeter put about a medical device because such a construction would tend to require precision not to dislodge the medical device when connected while maintaining a water resistant/water proof seal. Of course, planar embodiments of covers 20 or bubbles 10 (or not) could be employed with an access device 48 and/or a port 140 which are not believed to exist at this time.

One can quickly recognize the benefits of the goggle or bubble 10 over prior art constructions in being able to protect medical devices 12 without necessarily applying pressure to the medical device 12 preferably without any bands which might otherwise be looped about body parts, such as a torso, a leg, an arm, etc. . . . . Not only can wet activities, like swimming, waterskiing, jet skiing, surfing, or other water related activities be enjoyed while limiting contact of external water with the medical device 12, but also physical activities like sports (basketball, tennis, and/or others) could be enjoyed with the medical device 12 more likely to be retained in position with the bubble 10 so that the user need not worry if it might be dislodged during those activities. Additionally, non-connected medical devices 12 may be protected so that one can get wet, such as in a shower or bath. By providing the bubble 10 in a single-use configuration, it may be provided in a per-unit packaging so as to be disposable after use.

Many embodiments of the bubble 10 will have an access device 48 such as a pull strip 50 connected to an internal line 52 which could be a string, wire, sheet or other material whereby when the pull strip 50 is pulled, the line 52 tears or otherwise opens the cover 20 at a desired location and/or amount so that one may relatively quickly access the cavity 35 and/or the medical device 12. Many embodiments of the goggle 10 will be at least water resistant, if not water proof.

Figure 2:
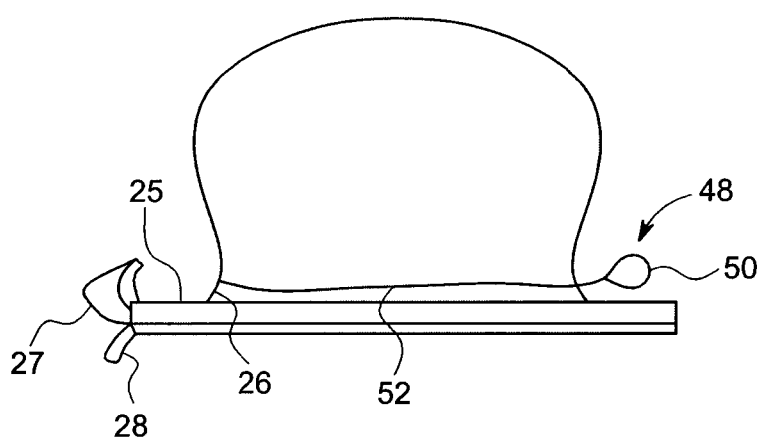
FIG. 2 is a side plan view of the embodiment of FIG. 1.
Figure 3:
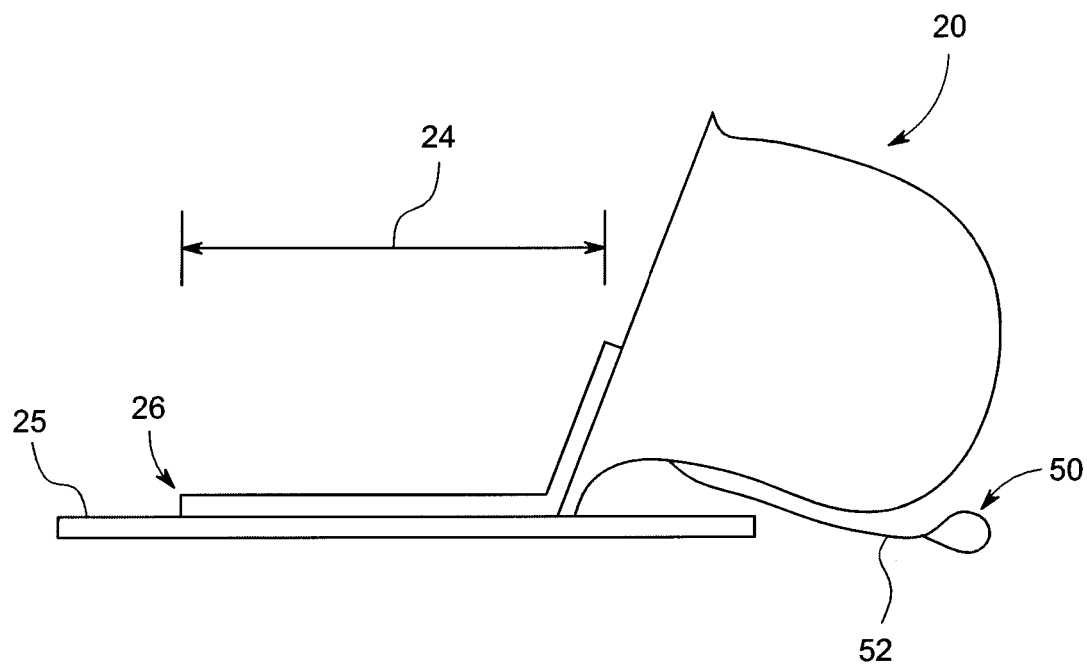
FIG. 3 is a side pan view of the embodiments of FIGS. 1 and 2 in an opened configuration.
Figure 4:
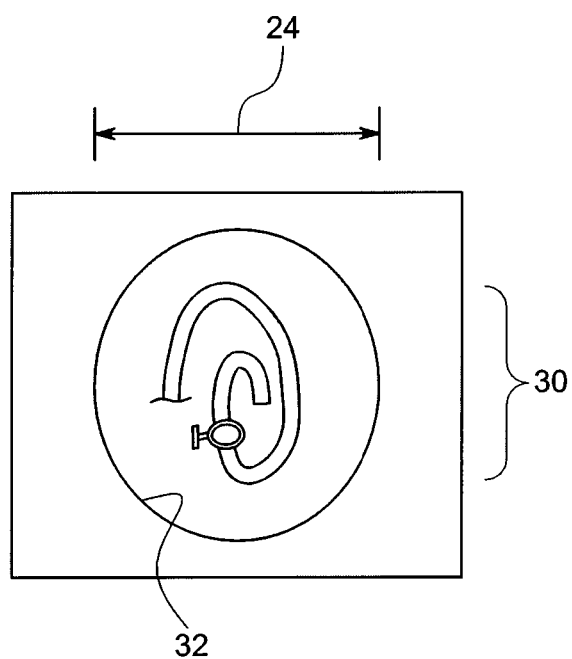
FIG. 4 is a top plan view of the embodiment of FIG. 1 installed on a from the user.
Figure 5:
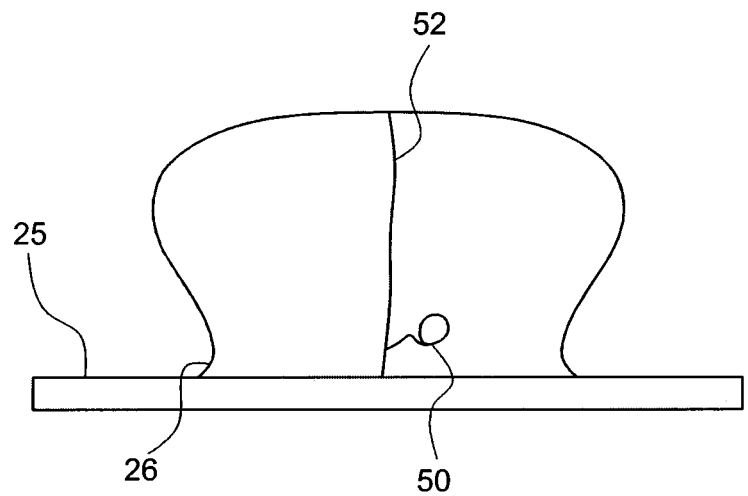
FIG. 5 is a side plan view of a first alternative embodiment similar to FIGS. 1-4.
Figure 6:
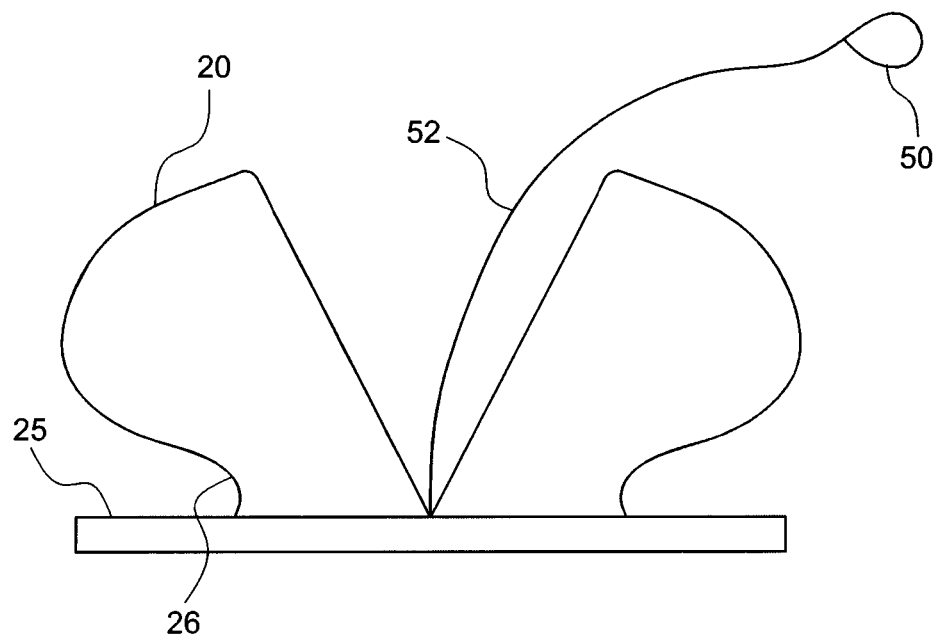
FIG. 6 is a side plan view similar to FIG. 5 in an opened configuration.

Some embodiments may have a laterally directed line 52 which may be parallel to base 25 as is shown in FIGS. 1-3. Other embodiments may have a vertically directed line 52 as is shown in FIGS. 5 and 6 which is perpendicular to the base 25. The embodiment of FIGS. 1-3 (FIG. 4 is generic to both) can be viewed as a ripping off of the cover 20 relative to the base 25 in an emergency or for removal of the goggle 10. The embodiment of FIGS. 5-6 has a line configured so that the cover 20 is somewhat split (like a clamshell as illustrated to provide access into the cavity 35. In the embodiment of FIGS. 1-3, the cover 20 may or may not be fully removed when activating the release mechanism or access device 48.

Figure 7:
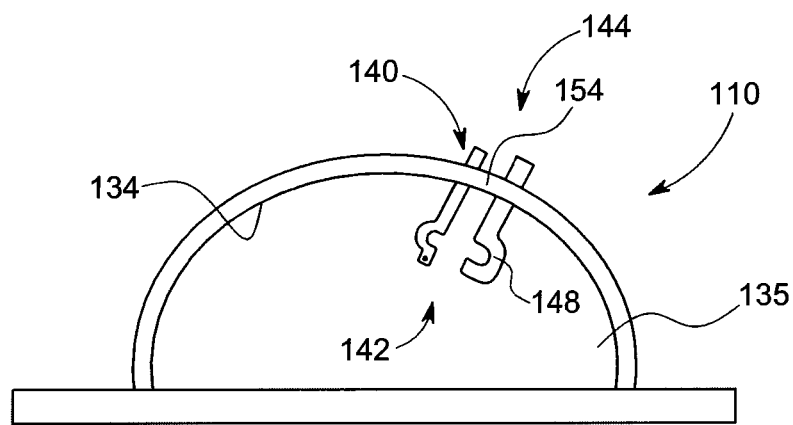
FIG. 7 is a cross sectional view similar to FIG. 1 with an optional port.
Figure 8:
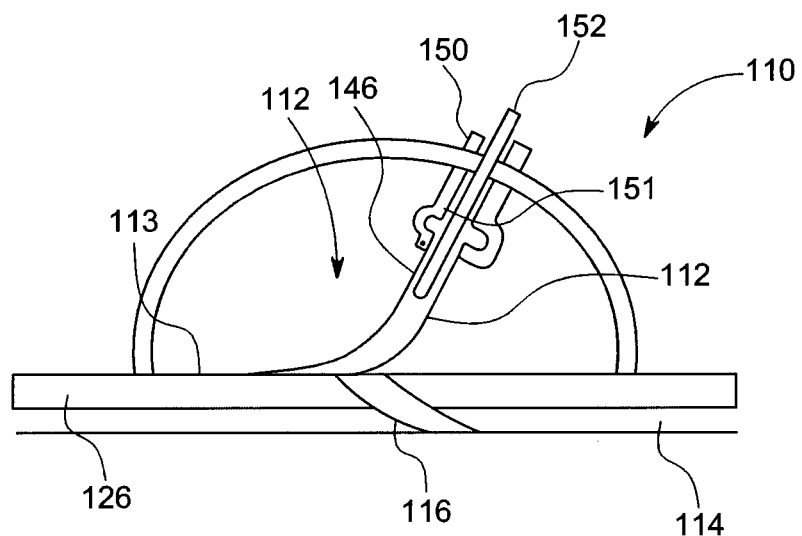
FIG. 8 is a cross sectional view showing the structure of FIG. 7 in an installed configuration.

FIGS. 7 and 8 show an alternatively preferred embodiment of a bubble 110 having an inner surface 134 defining a cavity 135 above the skin 114 of a user when installed, such as shown in FIG. 8. A port 140 can be provided which permits connection to a medical device at a first end 142 connected to the skin 114, such as with a needle 116. Port 140, for many embodiments, may have a first connection portion 148 which cooperates possibly with a connector 146 of a medical device 112, such, but not limited to an IV or other port or pic, which may, at least periodically, be connected to a fluid supply to provide fluids, medicine and/or other liquids to a patient through the medical device 112.

The connector 146 and first connection portion 148 can connect to secure the medical device 112 to the bubble 110 in the cavity 135. Outside the bubble 110, at least a guide, if not a second connection portion 150 can receive a needle 151 or other fluid supply 152 to direct fluid into the medical device 112 through the bubble 110. Some embodiments with ports 140 may be very simple, such as guides extending from interior and exterior surfaces of the bubble 110, while other may have integral valves, connectors and/or other structure. It may be that the bubble 110 has a resilient material at interface 154 which can reseal after use for at least some embodiments. Still other embodiments may have other features.

While many embodiments contemplate connecting a medical device 112 to a fluid supply 152 as a source through the goggle 110, some embodiments may communicate information through the port such as through a wire or other structure, if not wirelessly provided.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method of using a protective device comprising the steps of:
    covering a site with a bubble,
        said bubble comprising
            a cover, said cover extending over an upper most surface of the site external to the user and above a perimeter of the site when connected, an access device whereby upon activating the access device, the cover is opened while the base remains connected to the skin permitting access internal to the cover, the access device having a pull connected to a line, said line pulling through the cover to expose the site,
            and
            a foot having a predetermined inner perimeter connected to the cover and an initially planar base, said base adhering to the skin and forming at least a water-resistant connection against the skin of the user under the cover, said cover extending a distance beyond the inner perimeter of the foot when compressed; and
        securing the bubble to a body part with an adhesive at the base about the site, said site having a medical device connected to the user with the bubble providing a water resistant covering over the medical device.

2. The method of claim 1 wherein the site having the medical device has the medical device selected from the group of feeding tube connections, IV ports, insulin pumps, PODs, continuous glucose monitors, chemotherapy pumps, and glucose pumps.

3. The method of claim 2 where the seal is a waterproof seal.

4. The method of claim 3 further comprising a gap between the upper most surface of the medical device and the cover when covering the connected medical device with the bubble, with an air cavity located in the gap about the medical device.

5. The method of claim 1 wherein the cover is one of translucent and transparent and is non-planar with the base.

6. The method of claim 1 wherein the cover is one of flexible and rigid.

7. The method of claim 1 wherein the cover is spaced by a gap from the upper most surface of the medical device when covering the medical device.

8. The method of claim 1 wherein the foot of the cover against the skin forms a watertight seal.

9. The method of claim 1 wherein the cover is opened to fully expose the site in a fully opened configuration.

10. A method of using a protective device comprising the steps of:
    covering a site with a bubble,
        said bubble comprising
            a cover, said cover extending over an upper most surface of the site external to the user and above a perimeter of the site when connected, and
            a foot having a. predetermined inner perimeter connected to the cover and an initially planar base, said base forming at least a water-resistant connection against the skin of the user under the cover, said cover extending a distance beyond the inner perimeter of the foot when compressed; and
    a port along the bubble and further comprising the step of directing a fluid through the port into the medical device, the medical device having a connection which cooperates with a first connection portion of the port at least temporarily connecting the connection to the first connection portion, and a needle extending through the port into the medical device from external to the bubble, and securing the bubble to a body part with an adhesive at the base about the site, said site having a medical device connected to the user with the bubble providing a water resistant covering over the medical device.

\* \* \* \* \*